United States Patent [19]

Lewandowski

[11] Patent Number: 5,338,310

[45] Date of Patent: Aug. 16, 1994

[54] NEEDLE DEVICE HAVING SAFETY INDICATION FEATURES

[75] Inventor: Raymond D. Lewandowski, New Providence, N.J.

[73] Assignee: Becton, Dickinson and Company, Franklin Lakes, N.J.

[21] Appl. No.: 832,103

[22] Filed: Feb. 6, 1992

[51] Int. Cl.5 ............................................. A61M 5/32
[52] U.S. Cl. .................................. 604/192; 604/198; 604/110; 604/263
[58] Field of Search ........ 604/110, 111, 192, 194–198, 604/263; 128/919, 763, 202.22, 205.23; 206/364–366, 459.1

[56] References Cited

U.S. PATENT DOCUMENTS

| | | | |
|---|---|---|---|
| 2,801,741 | 8/1957 | Harkness et al. | 206/459.1 X |
| 4,285,105 | 8/1981 | Kirkpatrick | 206/459.1 X |
| 4,631,057 | 12/1986 | Mitchell | 604/198 |
| 4,723,943 | 2/1988 | Spencer | 604/198 |
| 4,747,837 | 5/1988 | Hauck | 604/198 |
| 4,801,295 | 1/1989 | Spencer | 604/198 |
| 4,840,185 | 6/1989 | Hernandez | 128/763 |
| 4,871,355 | 10/1989 | Kikkawa | 604/198 |
| 4,900,310 | 2/1990 | Ogle | 604/198 |
| 4,994,045 | 2/1991 | Ranford | 604/198 |
| 4,998,920 | 3/1991 | Johnson | 604/198 |
| 4,998,924 | 3/1991 | Ranford | 604/198 |
| 5,019,051 | 5/1991 | Hake | 604/198 |
| 5,045,066 | 9/1991 | Scheuble et al. | 604/198 |
| 5,053,018 | 10/1991 | Talonn et al. | 604/198 |
| 5,057,087 | 10/1991 | Harmon | 604/198 |
| 5,137,521 | 8/1992 | Wilkins | 604/198 |
| 5,147,303 | 9/1992 | Martin | 604/110 |
| 5,188,614 | 2/1993 | Hart | 604/197 |
| 5,197,953 | 3/1993 | Colonna | 604/110 |

*Primary Examiner*—C. Fred Rosenbaum
*Assistant Examiner*—Vanitha Alexander
*Attorney, Agent, or Firm*—John L. Voellmicke

[57] ABSTRACT

A safety needle device includes a barrel having an inside surface defining a chamber and an open proximal end. A distal end includes a needle cannula attached thereto. The needle cannula includes a distal tip and a lumen therethrough in fluid communication with the chamber. A needle guard is mounted on the barrel for movement relative to the barrel from a retracted position in which the needle guard does not materially obstruct access to the distal tip of the needle cannula and an extended position in which the needle guard obstructs access to the distal tip. The safety needle device includes structure for releasably retaining the needle guard in the retracted position and for locking the needle guard in the extended position. A safety indicator is provided on the distal end of the barrel for visually indicating that the needle guard is not in the locked extended position and an obscurement means is provided on the needle guard for obscuring or changing the appearance of the safety indicator when the needle guard is in the locked extended position.

16 Claims, 6 Drawing Sheets

NEEDLE DEVICE HAVING SAFETY INDICATION FEATURES

BACKGROUND OF THE INVENTION

1. Field of the Invention

The present invention relates to medical devices containing a needle cannula such as syringes, evacuated tube holders and the like. More particularly, the present invention relates to safety needle devices having self-contained safety shields which can be positioned to help prevent accidental contact with the needle point.

2. Description of Related Information

Generally speaking, a hypodermic syringe includes a cylindrical barrel, commonly made of thermoplastic material or glass, having a distal end connected to a sharpened needle cannula and a proximal end adapted to receive a stopper and plunger assembly.

In recent years there has developed an increased concern regarding the transfer of disease, infection or the like to syringe users and health-care professionals who accidentally stick themselves with hypodermic needles while disposing of used hypodermic syringe products. In many areas in a hospital, where needle cannula products are used, disposal bins are provided so that a syringe or other needle cannula product may be immediately discarded in a safe rigid container. However, there are areas of medical practice such as in emergency rooms, or other areas where disposal containers are not readily available or practical, where products having self-contained shielding devices are desirable. In theory, after the syringe is used to inject medication or for another purpose, a shield which surrounds the syringe barrel is advanced to an extended position and locked to prevent further contact with the sharp needle tip. The syringe, in this condition, can be safely transported to a disposal system.

Such a syringe is taught in U.S. Pat. No. 4,631,057 to Mitchell. This syringe contains a needle guard which is releasably retained in a retracted position, for allowing the syringe to be used for injection, and lockably retained in the extended position. To lock the needle guard in the extended position the user moves the needle guard axially distally along the syringe barrel until it snaps in the locked position. No further manipulation of the needle guard, such as rotation, is required.

A similar syringe is taught in U.S. Pat. No. 4,747,837 to Hauck. This patent teaches a syringe having a cylindrical sheath sleeve which can be advanced axially to a locked irreversible position which prevents further access to the needle cannula tip.

Other shielded syringe designs such as the syringe as taught in U.S. Pat. No. 4,998,920 to Johnson, U.S. Pat. No. 4,801,295 to Spencer and U.S. Pat. No. 5,053,018 to Talonn et al. allow the needle guard to be moved to a substantially fully extended position, through axial movement, without locking the needle guard. In this position, the syringe assembly appears to be safe, however, the needle guard can still be moved in a proximal direction to expose the sharp needle tip. These designs require an additional rotation of the needle guard, while the needle guard is fully extended, to place it in a locked position where it will not move proximally to expose the needle.

It can be seen, especially with designs requiring additional rotational movement of the needle guard to lock the needle guard in the extended position, that the syringe and needle guard assembly may appear to be safe to the user but the user can not be sure of its locked condition without carefully experimenting with the syringe assembly to determine its status.

Other safety needle devices such as evacuated blood collection tube holders are being designed to overcome the same problems that syringes face with respect to shielding and disposal. U.S. Pat. No. 4,871,355 to Kikkawa teaches an injury resistant needle and blood collection tube holder having an outer protective tube which is movable axially between the position where the needle protrudes for venipuncture to a position wherein the needle is housed entirely within the new protective tube.

A similar blood sampling device with shield is taught in U.S. Pat. No. 4,840,185 to Hernandez wherein a protective shield moves over helical grooves to permit longitudinal movement of the shield into positions which expose the needle for venipuncture or to enclose the needle and protect the user from accidental needle sticks.

Although the prior art teaches products which enhance the safety of needle device users by allowing the needle to be safely covered by a needle guard after use, there still exists a need for a simple, straight forward, reliable, easily fabricated safety needle device which provides the user with clear visual indication that the needle guard is in a locked safe position or that, even though the needle is covered by the needle guard, the needle guard is not in a locked safe position.

SUMMARY OF THE INVENTION

A safety needle device of the present invention includes a barrel having an inside surface defining a chamber and an open proximal end. The barrel includes a distal end having a needle cannula attached thereto. The needle cannula includes a lumen therethrough in fluid communication with the chamber. The needle cannula projects distally outwardly from the distal end of the barrel and terminates a distal tip. A needle guard is mounted on the barrel for movement relative to the barrel from a retracted position in which the needle guard does not materially obstruct access to the distal tip of the needle cannula and an extended position in which the needle guard obstructs access to the distal tip. The safety needle device includes means for releasably retaining the needle guard in the retracted position and means for locking the needle guard in an extended position. A safety indicator is provided on the distal end of the barrel for visually indicating that the needle guard is not locked in the extended position and an obscurement means is provided on the needle guard for changing the appearance of the safety indicator or obscuring the safety indicator when the needle guard is in the locked extended position.

DETAILED DESCRIPTION

While this invention is satisfied by embodiments in many different forms, there are shown in the drawings and will be herein described in detail preferred embodiments of the invention with the understanding that the present disclosure is to be considered exemplary of the principles of the invention and it is not intended to limit the scope of the invention to the embodiments illustrated. The scope of the invention will be measured by the appended claims and their equivalents.

Adverting to FIGS. 1-6, a safety needle device such as syringe assembly 20 includes a barrel 21 having an inside surface 22 defining a chamber 23. Barrel 21 also includes open proximal end 25 and distal end 27 having a needle cannula 28 attached thereto. The needle cannula includes a lumen therethrough in fluid communication with chamber 23. The needle cannula projects distally outwardly from distal end 27 of the barrel terminating in distal tip 31. In this embodiment of the invention the distal tip is sharpened to facilitate use of the needle to pierce the skin for delivery of therapeutic liquids. Also, in this embodiment the needle cannula is part of a needle assembly which includes needle hub 30. The needle hub includes structure to frictionally engage the distal end of the barrel so that the needle cannula is removably attached to the barrel.

For the purposes of the description of the present invention, the term "distal end" is intended to refer to the end of the syringe assembly furthest from the person holding the syringe, whereas the term "proximal end" is intended to refer to the end closest to the holder of the syringe.

The syringe assembly of this embodiment preferably includes a stopper 43 slidably positioned in fluid-tight engagement inside barrel 21. The stopper is capable of moving fluid from chamber 23 through the lumen of needle cannula 28 upon its movement toward distal end 27 of the barrel. The stopper is capable of facilitating drawing of fluid into the chamber through the lumen upon its movement away from the distal end of the barrel. A plunger rod 44 having an elongate body portion 45 engages stopper 43 to facilitate operation of the stopper. Body portion 53 extends outwardly from open proximal end 25 of the barrel. Disc-shaped plunger rod flange 46 is provided as a convenient structure for applying force to the plunger rod with respect to the barrel.

A needle guard 32 is mounted on barrel 21 for movement relative to the barrel from a retracted position in which the needle guard does not materially obstruct access to distal tip 31 of the needle cannula and in extended position, as illustrated in FIGS. 3-6, in which the needle guard obstructs access to the distal tip of the needle cannula.

Syringe assembly 20 includes means for releasably retaining the needle guard in the retracted position. In this preferred embodiment the means for releasably retaining the needle guard in the retracted position includes collar 33 mounted on the distal end of the barrel. The collar includes flange-like projection 34 extending radially outwardly from the collar body. When the needle guard is in the retracted position, projection 34 is in frictional engagement with inwardly projecting axial ribs 35 of the needle guard. The diameter described by ribs 35 is slightly smaller than the diameter described by flange-like projection 34 so that there exists a frictional engagement between the projection and the needle guard when the needle guard is in the retracted position. This engagement is easily overcome with manual force. Releasable engagement of the needle guard in the retracted position can be accomplished with many other structures such as frictional engagement of the outside surface of the barrel by inwardly projecting structure on the needle guard. The specific structure described above is representative of these many possibilities.

Figure 1:
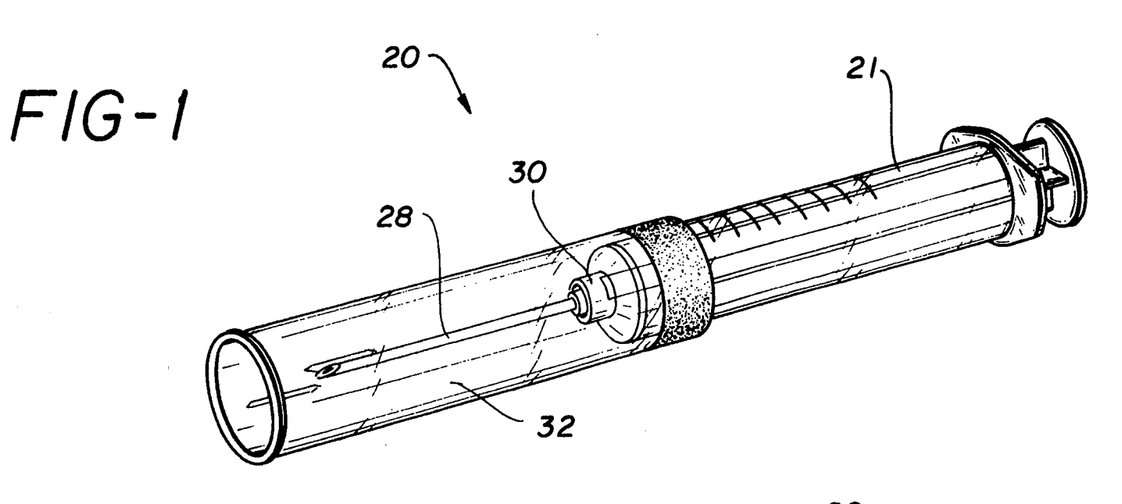
FIG. 1 is a perspective view of the preferred embodiment of the hypodermic syringe assembly of the present invention.
Figure 2:
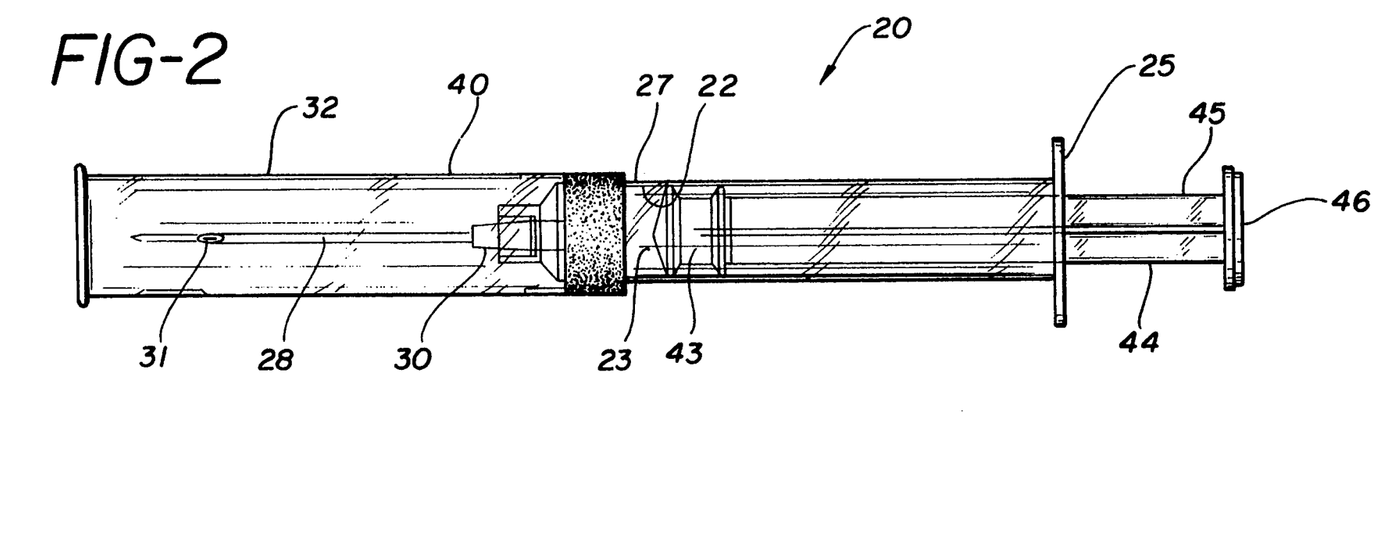
FIG. 2 is a side elevation view of the syringe assembly of FIG. 1.
Figure 3:
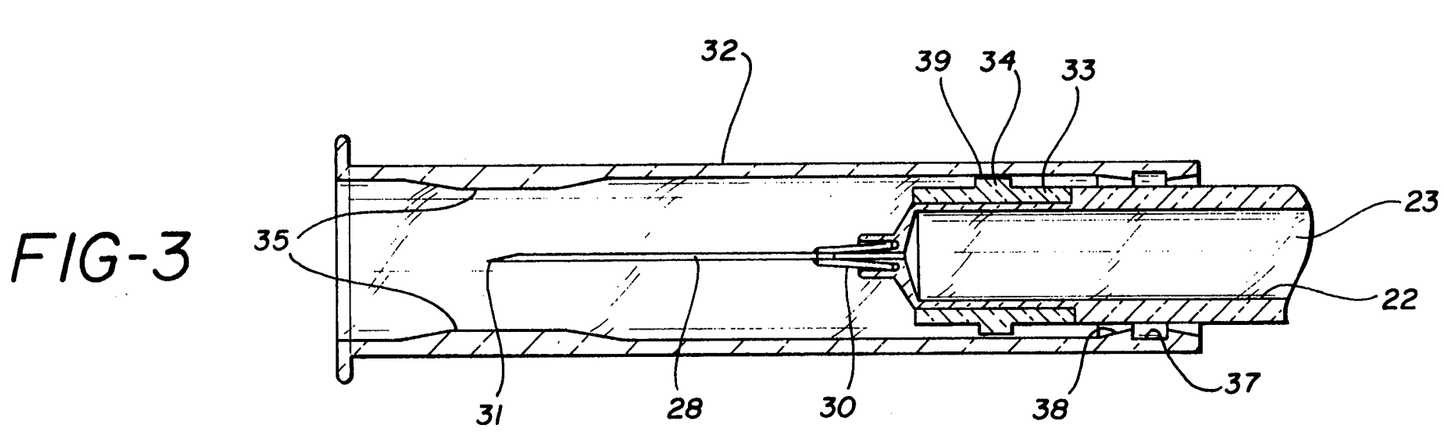
FIG. 3 is a partial cross-sectional view of the syringe assembly of FIG. 1 illustrating the needle guard in an extended unlocked position.
Figure 4:
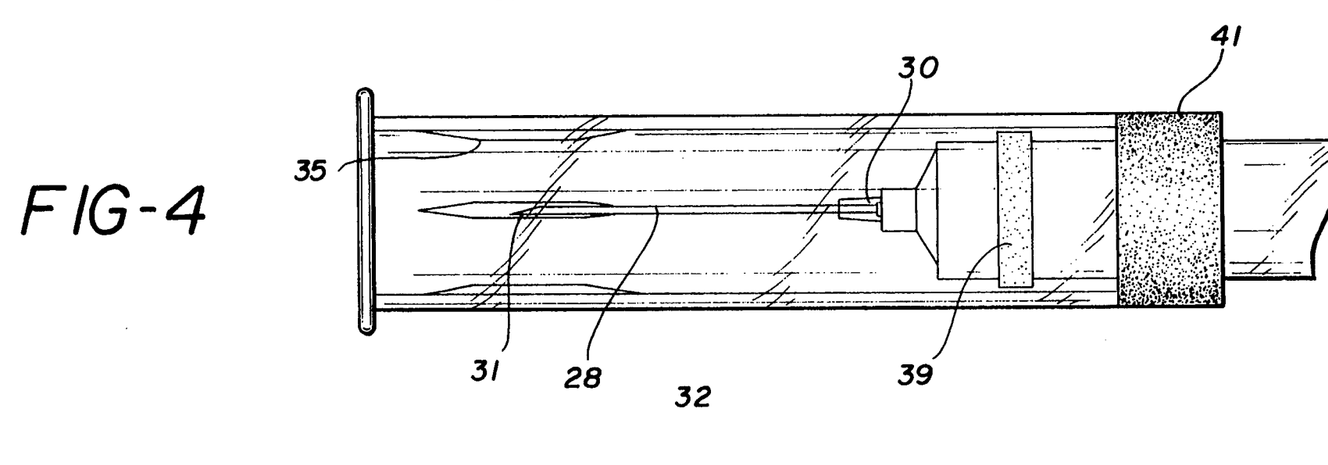
FIG. 4 is a partial side elevation view of the syringe assembly of FIG. 1 illustrating the needle guard in an extended unlocked position.
Figure 5:
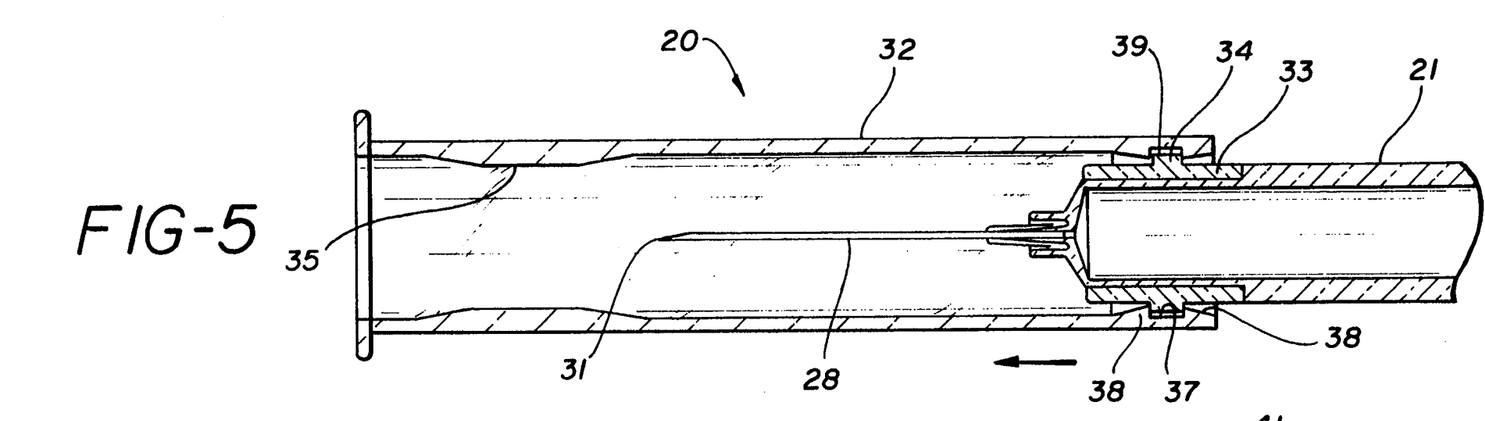
FIG. 5 is a partial cross-sectional view of the syringe assembly of FIG. 1 illustrating the needle guard in the fully extended locked position.
Figure 6:
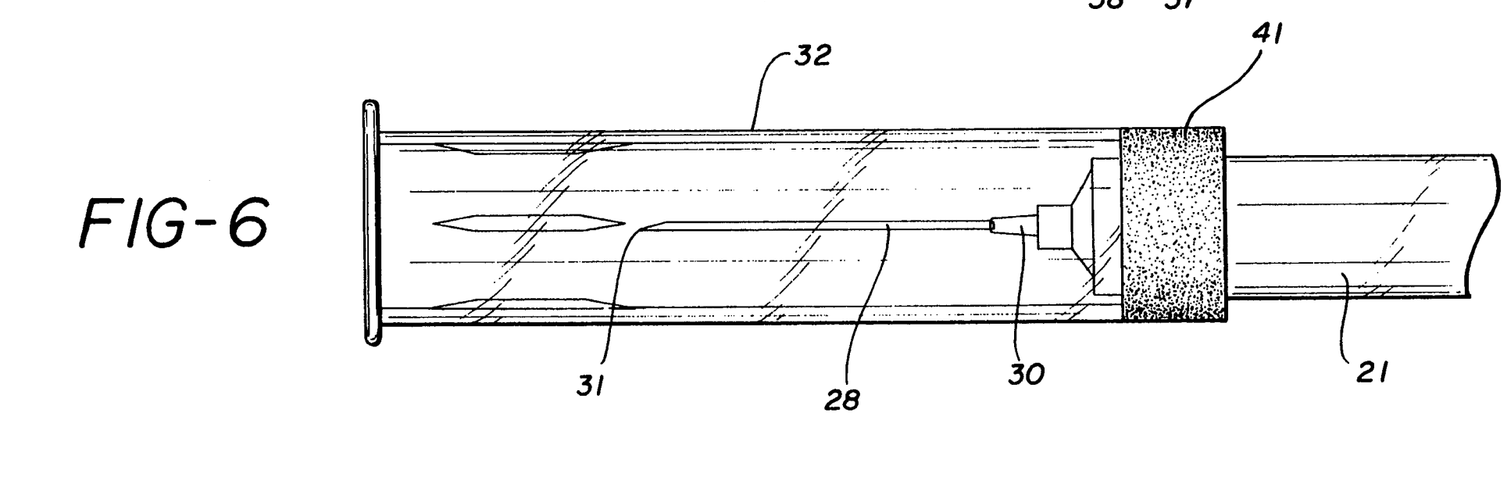
FIG. 6 is a partial side elevation view of the syringe of FIG. 1 showing the needle guard in the fully extended locked position.

Syringe 20 also includes means for locking the needle guard in the extended position in which the needle guard obstructs access to the distal tip of the needle. In this embodiment the means for locking the needle guard in the extended position includes interaction between projection 34 of collar 33 and recess 37 defined by inwardly projecting inclined plane projections 38. When the needle guard is moved distally with respect to the barrel an additional force is required to move the inclined plan projections over the projection 34 of the collar so that the projection snaps into recess 37 locking the collar and preventing further movement of the collar with respect to the barrel. The position of the needle guard in the extended locked position is best illustrated in FIGS. 5 and 6.

The syringe is safe for transporting to a disposal device when the needle guard is in its fully extended and locked position. The person who moves the needle guard to the extended locked position will know it is locked by feeling and/or hearing the locking means snap into engagement. However, in order to be sure that the needle guard is fully extended and locked, a person finding the syringe in an apparently safe locked condition would have to physically apply a force to the needle guard in a proximal direction to assure that it was locked. If the needle guard is not in a locked position it would move in a proximal direction with respect to the barrel further exposing the needle and possibly exposing the user to an accidental needle stick. The present invention provides a visual indication that the needle guard is in the extended and locked position without the need for further testing on the part of the user.

The present invention includes safety indicator means on the distal end of the barrel which visually indicates when the needle guard is not locked in the extended position. In this preferred embodiment the exterior surface 39 of projection 34 is coated with a printing ink or other coating in a color which preferably indicates a dangerous condition such as red. This circular red surface is visible through the transparent or translucent wall of the needle guard. The user knows that anytime the red band is visible that the needle guard is not securely locked in the extended needle protecting position.

The color marking on the syringe barrel can be placed anywhere along the barrel that is covered by the needle guard when the needle guard is in the fully extended position. Collar 33 could be molded in a colored plastic so that the need for further coating or printing is not necessary. Also, in this preferred embodiment side wall 40 of the needle guard is preferably transparent or translucent. The side wall may also be opaque with a translucent or transparent portion, or an opening, to enable visualization of the safety indicator.

The present invention also includes obscurement means on the needle guard for changing the appearance or obscuring the safety indicator when the needle guard is in the fully extended and locked position as illustrated in FIGS. 5 and 6. In this embodiment the obscurement means includes circumferential opaque band 41 printed on side wall 40 of the needle guard. Opaque band 41 is preferably wider in an axial direction than the safety indicator so that when the needle guard is in the full extended and locked position the circumferential opaque band will cover the safety indicator which is printed on the exterior surface 34 so that only the circumferential opaque band is visible to the user as best illustrated in FIG. 6. The circumferential opaque band can be made of a color which indicates safety such as green or any color or pattern which will obscure, render invisible or changes the appearance of the safety indicator on the exterior surface 34. It is possible to have a safety indicator in bright yellow and a translucent circumferential band in blue so that when the safety indicator and the circumferential band are aligned the color green will be visible to the user indicating a safe locked position. It is also possible to attach polarized film to the barrel and the needle guard to produce a visual change when the polarized portions are aligned. There are many combinations of transparent, translucent and opaque markings for the needle guard that can work in conjunction with the marking on the syringe barrel to indicate a potentially dangerous and a safe position to the user and the structures recited hereinabove are representative of these many possibilities.

Figure 7:
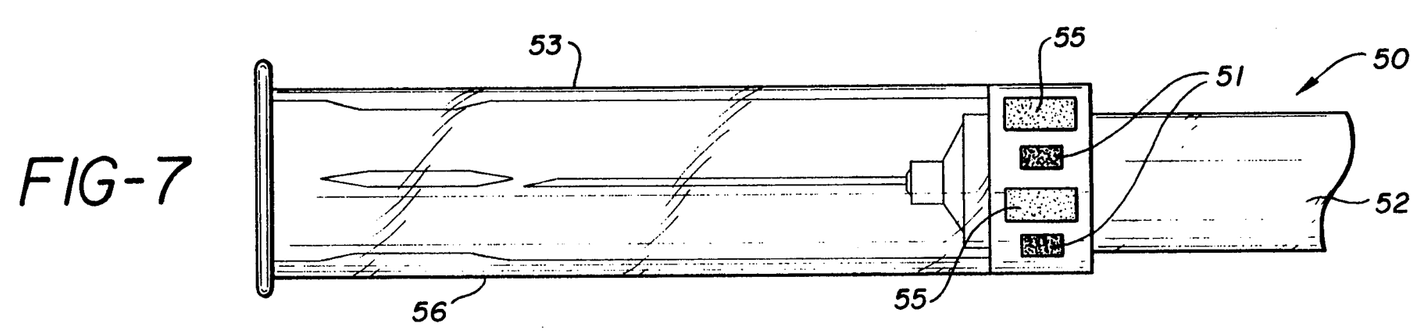
FIG. 7 is a partial side elevation view of a hypodermic syringe assembly having a shield mechanism of the twist and lock variety illustrated in an extended but not locked position.
Figure 8:
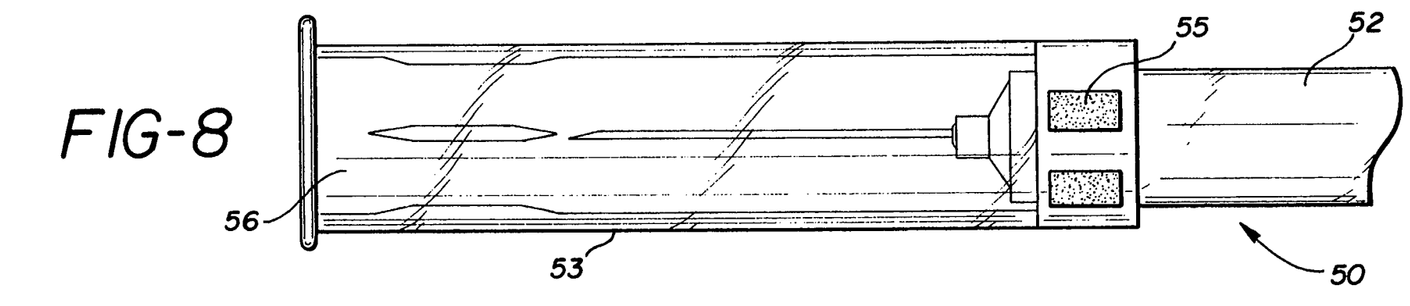
FIG. 8 is a partial side elevation view of a hypodermic syringe assembly of FIG. 7 in an extended locked position.

Referring to FIGS. 7–8, an alternative embodiment of the present invention is illustrated. This embodiment is intended for syringe structures wherein the needle guard is not necessarily locked in its fully extended position and must be rotated into a locked position. Such a syringe is taught in U.S. Pat. Nos. 4,801,295; 4,998,920; and No. 5,053,018. In this alternative embodiment syringe assembly 50 includes a safety indicator in the form of axial strips 51 printed on syringe barrel 52 which are visible through transparent needle guard 53. The axial strips are preferably printed in a color which indicates danger or an unsafe condition, such as bright red. The appearance of the red strips through the needle guard indicates a potentially unsafe condition to the user. The needle guard also includes obscurement means in the form of opaque strips 55 which may be printed on the exterior surface of needle guard side wall 56. Axial strips 55 may be printed in any color which obscures the color red when strips 55 are aligned with axial strips 51. The color green is preferred because it is generally construed as an indication of safety. When the needle guard of the syringe in the present embodiment is fully extended and rotated into a locked position, as best illustrated in FIG. 8, only axial strips 55 are visible to the user. The needle guard is then locked in a cannula protecting position and the user is informed of the locked status of the syringe assembly by the visual indication of the green axial strips. There are many possible variations of the indicators of the present invention. The needle guard may be transparent with opaque portions at its proximal end to obscure the safety indicators on the barrel. It is also possible to have an aperture in the needle guard which allows visualization of the safety indicator only when the needle guard is not in its extended locked position. All of these combinations fall within the purview of the present invention.

Figure 9:
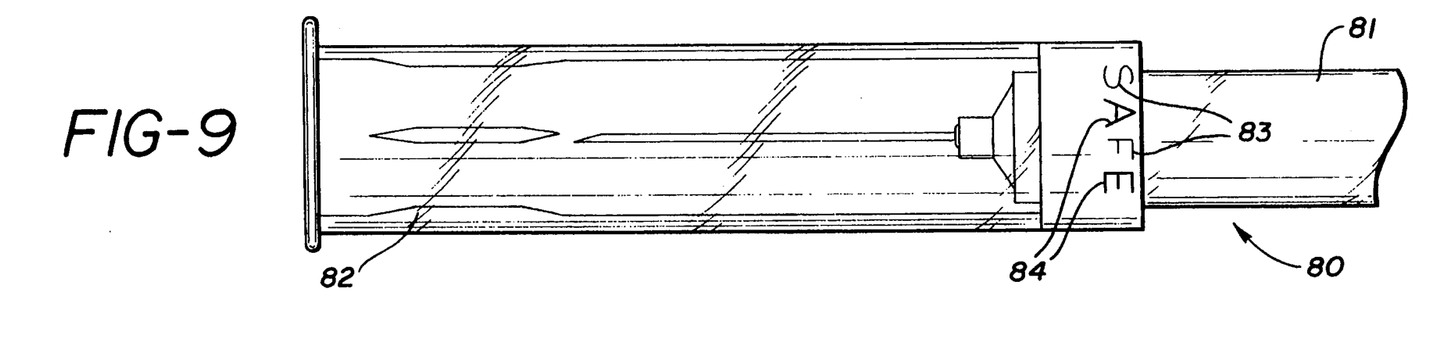
FIG. 9 is a partial side elevation view of an alternative embodiment of the syringe of FIG. 8.
Figure 10:
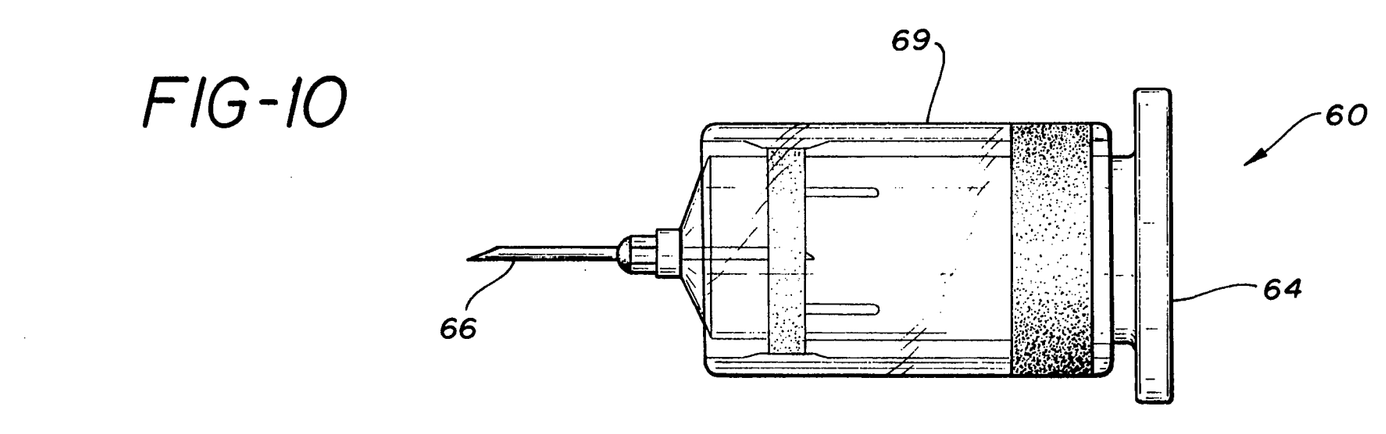
FIG. 10 is a side elevation view of a shielded evacuated tube holder.

As best illustrated in FIG. 9, the visual interaction between a syringe barrel 81 and a needle guard 82 of a syringe assembly 80 can also be used to provide a visual indication in the form of a word which indicates safety such as the word "safe." Two of the letters 83 of the word could be imprinted on the needle guard and two letters 84 could be printed on the syringe barrel so that only when a syringe is in a fully locked position will the word message indicating safety be visible. This embodiment is most suitable for needle devices where the needle guard must be rotated to lock it in the fully extended position similar to the syringe described in FIGS. 7–8.

Adverting now to FIGS. 10–13 an alternative embodiment of the present safety needle device comprises an evacuated blood collection tube holder 60 including a barrel 61 having an inside surface 62 defining a chamber 63. The barrel includes open proximal end 64 for accepting an evacuated blood collection tube (not illustrated) of the type having a cylindrical glass body with a closed proximal end and a pierceable rubber stopper sealing an open distal end. The barrel includes a distal end 65 having a needle cannula 66 attached thereto. The needle cannula includes a lumen therethrough in fluid communication with the chamber. The needle cannula projects distally outwardly from the distal end of the barrel and terminates in a sharpened distal tip 67. The needle cannula also includes a sharpened proximal tip 68 extending into chamber 63 for piercing the pierceable stopper of the evacuated blood collection tube.

Figure 11:
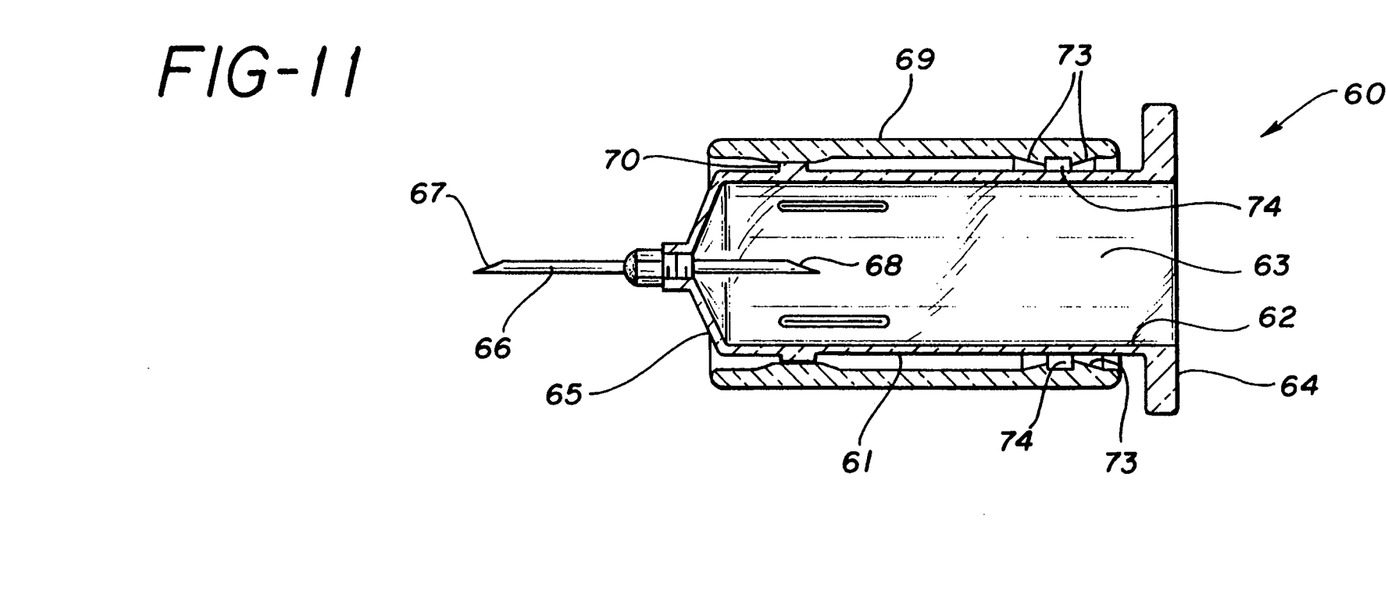
FIG. 11 is a cross-sectional view of the evacuated tube holder of FIG. 10.
Figure 12:
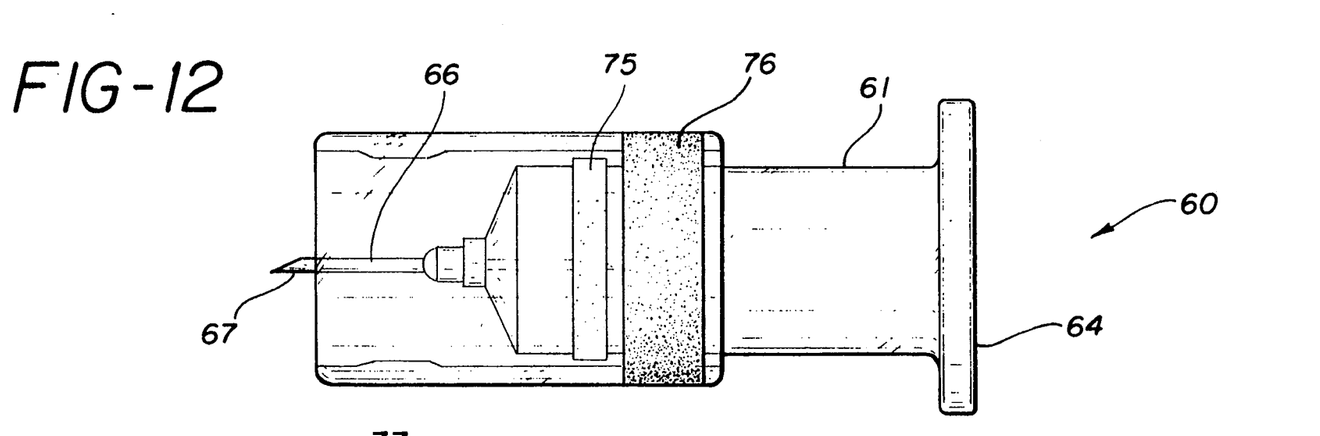
FIG. 12 is a side elevation view of the evacuated tube holder of FIG. 10 illustrating the needle guard in the extended unlocked position.
Figure 13:
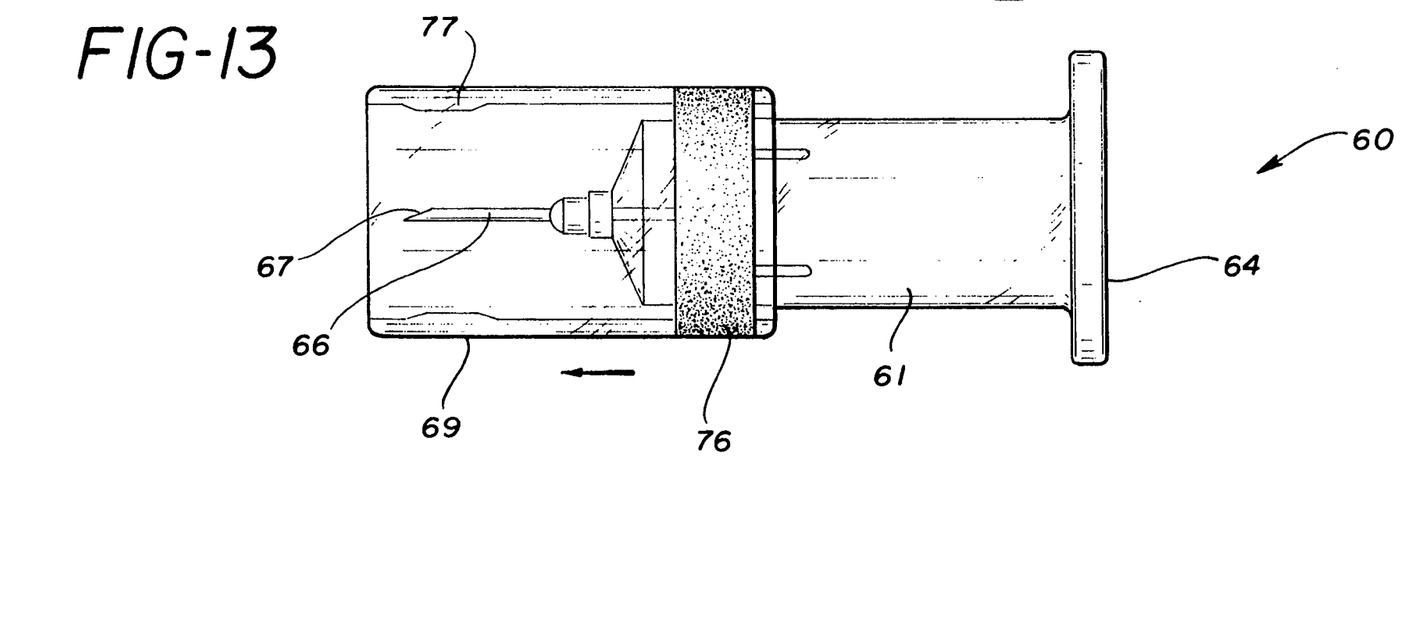
FIG. 13 is a side elevation view of the evacuated tube holder of FIG. 10 illustrating the needle guard in a fully extended locked position.

A needle guard 69 is mounted on the barrel for movement relative to the barrel from a retracted position in which the needle guard does not materially obstruct access to the distal tip of the needle cannula, as illustrated in FIG. 11, and in extended position in which the needle guard obstructs access to the distal tip of the needle as illustrated in FIG. 13.

The blood collection tube holder includes a radially projecting flange 70 at the distal end of the barrel which interacts with inwardly projecting ribs 71 on the distal end of the needle guard to releasably retain the needle guard in the retracted position.

The needle guard also includes inwardly projecting inclined plane projections 73 which define recess 74. When the needle guard is moved distally to the fully extended position the flange is forced by the most distal inclined plane projections and snaps into recess 74 to lock the needle guard in an extended position.

In this embodiment, the needle guard is transparent and the distal end of the barrel is printed with a circumferential band consisting of a colored coating to form safety indicator 75. The safety indicator is preferably in a color which indicates danger such as red, however, colors such as blue, red, orange or yellow are desirable with red being preferred. Before the needle guard is in the fully extended position the user can clearly see the safety indicator which indicates that the needle guard is not in a locked extended position. The needle guard also includes an obscurement means for obscuring the safety indicator or of changing the appearance of the safety indicator. In this embodiment the obscurement means consists of an annular opaque coating 76 on needle guard side wall 77. When the needle guard is in a fully extended locked position the annular opaque coating covers the safety indicator indicating to the user that the blood collection tube holder is safe because the needle guard is in a fully extended locked position. Annular coating 76 can be a colored segment desirably of green, black, blue or white with green and black being preferred. The annular coating 76 may also be translucent so that it changes the appearance of the safety indicator colors such as blue and green are desirable.

The barrel of the needle device of the present invention may be constructed of a wide variety of rigid materials with glass and thermoplastic materials such as polypropylene and polyethylene being preferred. Similarly, thermoplastic materials such as polypropylene, polyethylene and polystyrene are desirable for the plunger rod of the syringe embodiment. A wide variety of materials such as natural rubber, synthetic rubber and thermoplastic elastomers are suitable for the stopper of the syringe embodiment. A wide variety of commercially available inks may be used to form the safety indicator on the barrel and the obscurement means on the needle guard. The inks and/or coatings usable for the instant invention should be of medical grade quality. The colors may also be molded into the parts. For embodiments of the present invention which are desirably sterile the materials used for the components should be chosen to withstand the sterilization process utilized.

Thus, it can be seen that the present invention provides a simple, straight-forward, reliable, easily fabricated needle device which provides the user with clear visual indication that the needle guard is in a locked safe position or that, even though the needle is covered by the needle guard, the needle guard is not in a locked safe position.

What is claimed is:

1. A safety needle device comprising:
   a barrel having an inside surface defining a chamber, an open proximal end, a distal end having a needle cannula attached thereto, said needle cannula having a lumen therethrough in fluid communication with said chamber, said needle cannula projecting distally outwardly from said distal end of said barrel and terminating in a distal tip;
   a needle guard mounted on said barrel for movement relative to said barrel from a retracted position in which said needle guard does not materially obstruct access to said distal tip of said needle cannula and an extended position in which said needle guard obstructs access to said distal tip;
   means for releasably retaining said needle guard in said retracted position;
   means for locking said needle guard in said extended position;
   safety indicator means on said distal end of said barrel for visually indicating that said needle guard is not locked in said extended position; and
   obscurement means on said needle guard for changing the appearance or obscuring said safety indicator means when said needle guard is in said locked extended position, said obscurement means including a colored segment including a substantially opaque portion positioned to cover said safety indicator means when said needle guard is locked in the extended position.

2. The safety needle device of claim 1 wherein said safety indicator means includes a colored segment.

3. The safety needle device of claim 2 wherein said colored segment of said safety indicator means is shaped to form at least one alphanumeric character.

4. The safety needle device of claim 2 wherein said colored segment of said safety indicator means is a color selected from the group consisting of black, blue, red, orange and yellow.

5. The safety needle device of claim 4 wherein said colored segment of said safety indicator means is an annular ring.

6. The safety needle device of claim 1 wherein said opaque portion of said colored segment is a color selected from the group consisting of green, black, blue and white.

7. The safety needle device of claim 1 wherein said means for locking includes a collar mounted on said distal end of said barrel and interlocking means on said collar and said needle guard for locking said needle guard in said extended position.

8. The safety needle device of claim 1 wherein said needle cannula is removably attached to said barrel.

9. The safety needle device of claim 1 wherein said needle cannula includes a proximal sharp end extending into said chamber.

10. The safety needle device of claim 1 wherein said barrel is a syringe barrel having a stopper slidably positioned in fluid-tight engagement inside said barrel, said stopper capable of moving fluid from said chamber through said lumen upon its movement toward said distal end, said stopper capable of facilitating the drawing of fluid into said chamber through said lumen upon its movement away from said distal end.

11. The safety needle device of claim 1 wherein said colored segment of said obscurement means is shaped to form at least one alphanumeric character.

12. A safety device comprising:
   a syringe barrel having an inside surface defining a chamber, an open proximal end, a distal end having a needle cannula attached thereto, said needle cannula having a lumen therethrough in fluid communication with said chamber, said needle cannula projecting distally outwardly from said distal end of said barrel and terminating in a distal tip;
   a stopper slidably positioned in fluid-tight engagement inside said barrel, said stopper capable of moving fluid from said chamber through said lumen upon its movement toward said distal end, said stopper capable of facilitating the drawing of fluid into said chamber through said lumen upon its movement away from said distal end;
   a needle guard mounted on said barrel for movement relative to said barrel from a retracted position in which said needle guard does not materially obstruct access to said distal tip of said needle cannula and an extended position in which said needle guard obstructs access to said distal tip;

means for releasably retaining said needle guard in said retracted position;

means for locking said needle guard in said extended positions said means for locking including a collar mounted on said distal end of said barrel and interlocking means on said collar and said needle guard for locking said needle guard in said extended position;

safety indicator means on said distal end of said barrel for visually indicating that said needle guard is not locked in said extended position, said safety indicator means including a colored segment;

obscurement means on said needle guard for changing the appearance or obscuring said safety indicator means when said needle guard is in said locked extended position, said obscurement means including a substantially opaque segment positioned to cover said safety indicator means when said needle guard is in said locked extended position.

13. The safety needle device of claim 12 wherein said colored segment of said safety indicator means is selected from the group consisting of black, blue, red, orange yellow.

14. The safety needle device of claim 12 wherein said opaque segment is a colored segment.

15. The safety needle device of claim 12 wherein said obscurement means is shaped to form at least one alpha numeric character.

16. The safety device of claim 12 wherein said color segment of said safety indicator means is shaped to form at least one alpha numeric character.

* * * * *